US011911129B2

United States Patent
Hoppe et al.

(10) Patent No.: US 11,911,129 B2
(45) Date of Patent: Feb. 27, 2024

(54) METHOD AND DEVICE FOR DETERMINING A CARDIAC PHASE IN MAGNET RESONANCE IMAGING

(71) Applicant: Siemens Healthcare GmbH, Erlangen (DE)

(72) Inventors: Elisabeth Hoppe, Erlangen (DE); Jens Wetzl, Spardorf (DE); Seung Su Yoon, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 335 days.

(21) Appl. No.: 17/191,896

(22) Filed: Mar. 4, 2021

(65) Prior Publication Data

US 2021/0287364 A1    Sep. 16, 2021

(30) Foreign Application Priority Data

Mar. 12, 2020    (EP) .................................... 20162742

(51) Int. Cl.
*G06T 7/00* (2017.01)
*A61B 5/00* (2006.01)
(Continued)

(52) U.S. Cl.
CPC ............ *A61B 5/0044* (2013.01); *G06N 3/08* (2013.01); *G06T 7/0012* (2013.01); *G16H 30/20* (2018.01);
(Continued)

(58) Field of Classification Search
CPC ......... G06T 7/0012; G06T 2207/10088; G06T 2207/20081; G06T 2207/20084;
(Continued)

(56) References Cited

U.S. PATENT DOCUMENTS

| | | | |
|---|---|---|---|
| 2013/0187652 A1 | 7/2013 | Hu et al. | |
| 2015/0309135 A1* | 10/2015 | Axel ................ | G01R 33/56509 324/309 |

(Continued)

OTHER PUBLICATIONS

Pang, J. et. al.: "ECG and Navigator-Free Four-Dimensional Whole-Heart Coronary MRA for Simultaneous Visualization of Cardiac Anatomy and Function", in: Magnetic Resonance in Medicine 2014, vol. 72, pp. 1208-1217.
(Continued)

*Primary Examiner* — Van D Huynh
(74) *Attorney, Agent, or Firm* — Harness, Dickey & Pierce, P.L.C.

(57) ABSTRACT

A trained deep learning network is for determining a cardiac phase in magnet resonance imaging. In an embodiment, the trained deep learning network includes an input layer; an output layer; and a number of hidden layers between input layer and output layer, the layers processing input data entered into the input layer. In an embodiment, the deep learning network is designed and trained to output a probability or some other label of a certain cardiac phase at a certain time from entered input data. A method for determining a cardiac phase in magnet resonance imaging; a related device; a training method for the deep learning network; a control device and a related magnetic resonance imaging system are also disclosed.

27 Claims, 4 Drawing Sheets

(51) Int. Cl.
*G06N 3/08* (2023.01)
*G16H 30/20* (2018.01)

(52) U.S. Cl.
CPC .............. *G06T 2207/10088* (2013.01); *G06T 2207/20081* (2013.01); *G06T 2207/20084* (2013.01); *G06T 2207/30048* (2013.01)

(58) Field of Classification Search
CPC ............ G06T 2207/30048; G06N 3/08; G16H 30/20; G01R 33/4824; G01R 33/5608; G01R 33/56509; G01R 33/5676; G01R 33/56325; A61B 5/0044; A61B 5/7267; A61B 5/7289; A61B 2576/023; A61B 5/055
USPC ........................................................ 382/131
See application file for complete search history.

(56) References Cited

U.S. PATENT DOCUMENTS

| | | | |
|---|---|---|---|
| 2015/0374237 | A1 | 12/2015 | Hu et al. |
| 2018/0259608 | A1* | 9/2018 | Golden ............ G01R 33/56308 |
| 2019/0154785 | A1* | 5/2019 | Zhou ................ G01R 33/56316 |
| 2020/0022660 | A1* | 1/2020 | Sha ...................... A61B 5/0044 |
| 2020/0026967 | A1* | 1/2020 | Kartoun ............. G01R 33/4818 |
| 2020/0085394 | A1* | 3/2020 | Turcea ................... A61B 5/352 |
| 2020/0107818 | A1* | 4/2020 | Keshet ................. A61B 8/0883 |
| 2020/0134889 | A1* | 4/2020 | Govari ............... G01R 33/5676 |
| 2021/0219862 | A1* | 7/2021 | Loecher ................. A61B 5/318 |
| 2021/0267455 | A1* | 9/2021 | Ghadimi ................ G16H 30/40 |
| 2021/0350179 | A1* | 11/2021 | Bello .................. G06F 18/2148 |

OTHER PUBLICATIONS

Usman, M. et. al., "Free breathing whole-heart 3D CINE MRI with self-gated Cartesian trajectory", Magnetic resonance imaging 38: 129-137, 2017.

Odille Freddy et al; "Model-Based Reconstruction for Cardiac Cine MRI Without ECG or Breath Holding" Magnetic Resonance in Medicine, vol. 63, pp. 1247-1257, 2010.

Speier, P. et al. "PT-Nav: A Novel Respiratory Navigation Method for Continuous Acquisition Based on Modulation of a Pilot Tone in the MR-Receiver" ESMRMB 129:97-98, 2015 // DOI: 10.1007/s10334-015-0487-2.

Hoppe, E. et. al., "DeepECG: Towards 3-D Continuous Cardiac MRI without ECG-Gating—Deep Learning based R-Wave Classification for Automated Cardiac Phase Binning", submitted to the Annual ISMRM Meeting, 2020.

Di Sopra, L. et. al., "Motion-Resolved 5D Imaging of the Heart: Time to Get Rid of the ECG?", Proceedings of the 25th ISMRM Annual Meeting, Abstract 3148, 2017.

Di Sopra, L. et. al., "An automated approach to fully self-gated free-running cardiac and respiratory motion-resolved 5D whole-heart MRI", Magnetic resonance in medicine 82.6: 2118-2132, 2019.

Kong Bin et al: "Recognizing End-Diastole and End-Systole Frames via Deep Temporal Regression Network", 2016, 12th European Conference on Computer Vision, ECCV 2012; [ Lectu re Notes in Computer Science], pp. 264-272, XP047527543, ISSN: 0302-9743 ISBN: 978-3-642-36741-0 * the whole document*.

Feng, Li et al. "5D Whole-Heart Sparse MRI", Magnetic Resonance in Medicine, 2018, vol. 79, pp. 826-838.

Hoppe, E. et. al., "Free-Breathing, Self-Navigated and Dynamic 3-D Multi-Contrast Cardiac CINE Imaging Using Cartesian Sampling and Compressed Sensing", Proceeding of the 27th Annual ISMRM Meeting, Abstract 2129, 2019.

Wetzl, Jens et al.: "Free-Breathing, Self-Navigated Isotropic 3-D CINE Imaging of the Whole Heart Using Cartesian Sampling"; in: Proc. Intl. Soc. Mag. Reson. Med.; vol. 24; 2016; abstract No. 411.

Debus Alejandro et al: "Left Ventricle Quantification Through Spatio-Temporal CNNs", Feb. 14, 2019 (Feb. 14, 2019), Advances in Databases and Information Systems; [Lecture Notes in Computer Science; Lect.Notes Computer], Springer International Publishing, Cham, pp. 466-475, XP047505076, ISBN: 978-3-319-10403-4 [retrieved on Feb. 14, 2019] * figures 2,3 *.

Yerly, J. et. al., "Fully Self-Gated Cardiac and Respiratory Motion-Resolved 5D MRI for Rapid Assessment of Left Ventricular Function", Proceedings of the 27th ISMRM Annual Meeting. Abstract 2106, 2019.

Wufeng Xue et al: "Full left ventricle quantification via deep multitask relationships learning", Medical Image Analysis, vol. 43, Sep. 28, 2017 (Sep. 28, 2017), pp. 54-65, XP055723267, GB ISSN: 1361-8415, DOI: 10.1016/j.media.2017.09.005 * figures 2,5 *.

European Search Report dated Aug. 28, 2020.

* cited by examiner

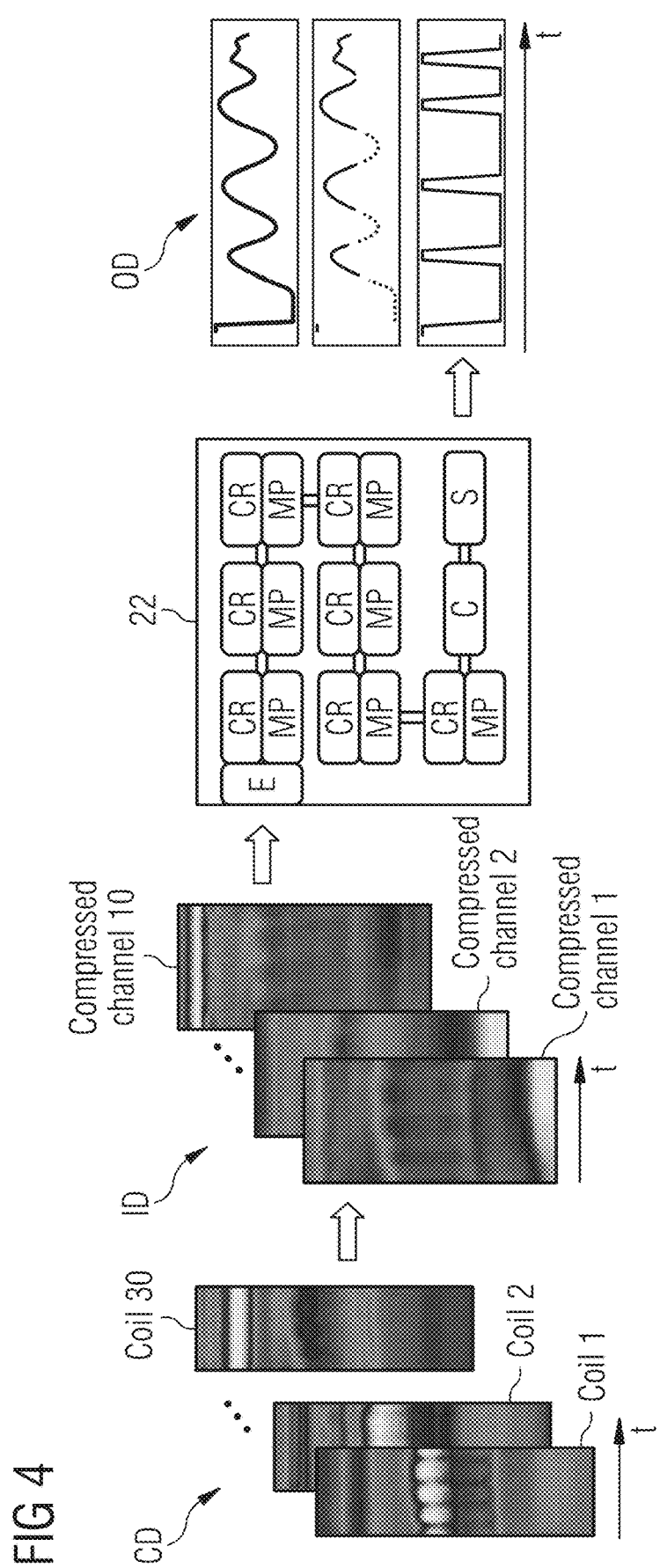

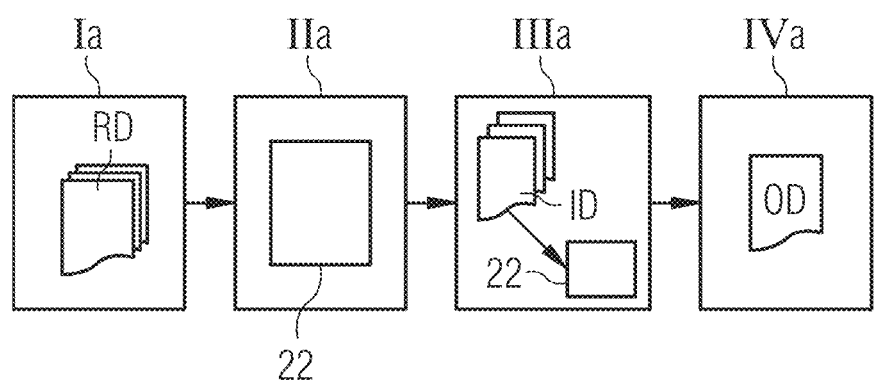

METHOD AND DEVICE FOR DETERMINING A CARDIAC PHASE IN MAGNET RESONANCE IMAGING

PRIORITY STATEMENT

The present application hereby claims priority under 35 U.S.C. § 119 to European patent application number EP20162742.9 filed Mar. 12, 2020, the entire contents of which are hereby incorporated herein by reference.

FIELD

Example embodiments of the invention describe a method and a device for determining a cardiac phase in magnet resonance imaging, especially for R-wave or ECG classification for automated self-navigated retrospective cardiac binning based on deep learning.

BACKGROUND

Cardiac dynamic magnetic resonance images, so-called CINE images, can be used to examine the cardiac cycle and the movement of the anatomical structures during a cardiac cycle (see e.g. Usman, M., et al. "Free breathing whole-heart 3D CINE MRI with self-gated Cartesian trajectory Magnetic resonance imaging 38 (2017): 129-137).

To acquire these dynamic images of the heart, the whole cardiac cycle has to be sampled during an imaging acquisition (see e.g. Pang, Jianing, et al. "ECG and navigator-free four-dimensional whole-heart coronary MRA for simultaneous visualization of cardiac anatomy and function" Magnetic resonance in medicine 72.5 (2014): 1208-1217 or Yerly, Jerome, et al. "Fully Self-Gated Cardiac and Respiratory Motion-Resolved 5D MRI for Rapid Assessment of Left Ventricular Function", Proceedings of the 27 ISMRM Annual Meeting; Abstract 2106. 2019.).

In most cases, this cannot be done in real-time, which would mean to acquire one whole image or volume during a short period within the cardiac cycle.

Using so-called segmented acquisition approaches, the k-space is sampled partly during one cardiac phase, and other parts of the k-space are acquired later during subsequent heart beats. This way, the sampled k-space for the reconstruction of one cardiac phase is acquired within multiple heart beats and at different time points during the measurement. Such acquisitions can be implemented as continuous sequences, where data is acquired continuously during free-breathing over multiple heart beats and independently of cardiac or respiratory phases.

After the measurement, data is retrospectively binned into different cardiac phases and multiple cardiac phases are reconstructed, resulting in dynamic images (CINE images). In order to reconstruct these CINE images or other 2D images or 3D volumes, it is essential to know the actual position of every acquired data sample or k-space line within a heartbeat, thus, to be able to assign the correct cardiac phase to a data sample for the reconstruction.

State-of-the-art acquisitions use two main directions to solve this binning: First, Electrocardiogram (ECG) signal is recorded along with the continuous sequence (see e.g. Feng, Li, et al. "5D whole-heart sparse MRI" Magnetic resonance in medicine 79.2 (2018): 826-838, Wetzl, Jens, et al. "Free-Breathing, Self-Navigated Isotropic 3D CINE Imaging of the Whole Heart Using Cartesian Sampling", Proceedings of the 24 Annual ISMRM Meeting; Abstract 411. 2016 or Hoppe, Elisabeth, et al. "Free-Breathing, Self-Navigated and Dynamic 3-D Multi-Contrast Cardiac CINE Imaging Using Cartesian Sampling and Compressed Sensing"; Proceeding of the 27 Annual ISMRM Meeting; Abstract 2129; 2019).

From this signal, the distance to the previous R-wave for every sampled data point or k-space line in time can be reached and be used to bin the data. Second, methods like Principal Component Analysis (PCA) or Independent Component Analysis (ICA) in combination with frequency filtering are implemented to recognize the cardiac movement from the measured data itself, without the need for an ECG-signal.

These methods typically use so-called 1D Superior-Inferior projections (SI), which are 1D projections from the central k-space line of the imaged volume at a timepoint t. For acquisitions using sampling techniques which repeatedly acquire the k-space center line in SI direction (e.g. radial or Cartesian sampling), these sampled centered k-space lines can be used to exploit movements during the acquisition, e.g. the cardiac movement. Thus, these movements and different states within a cardiac cycle can be derived from the data itself without an external ECG-signal.

The state-of-the-art methods for the derivation of cardiac phases for the acquired k-space lines can be separated into two main approaches:

1) Using an additionally acquired external signal, e.g. from an ECG, a pulse sensor or pilot tone/BEAT sensor (see e.g. Speier et al. "PT-Nav: a novel respiratory navigation method for continuous acquisitions based on modulation of a pilot tone in the MR-receiver" Proceedings from the European Society for Magnetic Resonance in Medicine and Biology, Edinburgh, United Kingdom (2015): 128).

For this approach, the cardiac movement is recorded using an external ECG-signal simultaneously with the MR signal during the continuous acquisition. The ECG device is placed on the patient prior to the measurement and the ECG-signal is recorded during the whole acquisition. Thus, the position of one acquired data point or k-space line within a cardiac heartbeat is known with the temporal resolution of the ECG-signal.

2) Using the data itself and analyzing it with postprocessing methods based on ICA/PCA. This second approach is used to derive the cardiac movements and the positions of R-waves from the central k-space lines themselves, without using an additional and external ECG-signal.

Prior to the R-wave extraction/detection, the signals have to be filtered to remove e.g. trajectory-dependent imperfections or noise from the data to prevent their influence on the subsequent computations. Afterwards, the central k-space readouts are processed using approaches based on PCA or ICA. In order to extract the cardiac motion, one example is to select components in a specific frequency range from the power spectral densities of the main principal or independent components. This range has to be known a priori.

Another option is to analyze the magnitude of the central coefficient of each 1D-SI readout (k0-modulation, see e.g. Di Sopra, Lorenzo, et al. "An automated approach to fully self-gated free-running cardiac and respiratory motion-resolved 5D whole-heart MRI" Magnetic resonance in medicine 82.6 (2019): 2118-2132 or Di Sopra, Lorenzo, et al. "Motion-Resolved 5D Imaging of the Heart: Time to Get Rid of the ECG?" Proceedings of the 25 ISMRM Annual Meeting; Abstract 3148; 2017) and to apply similar frequency filtering as for PCA and ICA approaches. The timepoints of R-waves, or more general the same relative positions within the cardiac cycle in each heartbeat, are then extracted from the derived curves of principal/independent components.

SUMMARY

The inventors have discovered that the above is not necessarily related to the electrical activity of the heart and could also be the mechanical activity that can be seen in the images.

At least one embodiment of the present invention is directed to improving the known systems, devices and methods to facilitate an improvement in detecting a cardiac phase, and especially easily facilitate retrospective cardiac binning.

Embodiments are directed to a trained deep learning network, a method, a device, a training method, a control device and a magnetic resonance imaging system.

A trained deep learning network according to an embodiment of the invention for determining a cardiac phase in magnet resonance imaging comprises an input layer, an output layer and a number of hidden layers between input layer and output layer and the layers processing input data entered into the input layer. The deep learning network is designed and trained to output a probability or some other label of a certain cardiac phase at a certain time from entered input data. This means that the output of the deep learning network is a probability in dependence on time or a label (i.e. the dependence) for certain time points of a dataset.

A training method according to an embodiment of the invention for manufacturing a deep learning network according to the invention, comprises:
a) providing a deep learning network intended to be trained, wherein the deep learning network is designed to output a probability or other label of a certain cardiac phase at a certain time from input data;
b) providing multiple training-datasets, based on MRI-measurements of the heart over a predefined measuring-time period and information about a predefined cardiac phase at certain time points of each training-dataset as ground truth, the information especially based on ECG data;
c) entering a training-dataset into an input layer of the deep learning network;
d) calculating a loss-value based on the difference between the output of the deep learning network and the information about the predefined heart phase within a synchronized time from the ground-truth;
e) adjusting parameters of the deep learning network;
f) repeating steps d) and e) until the loss-value suits a convergence criterium (e.g. is below a predefined threshold) or the maximum number of repetitions is reached; and
g) repeating steps c) to f) multiple times for different training-datasets.

A method according to an embodiment of the invention for (automatically) determining a cardiac phase in magnet resonance imaging can also be used for controlling a magnetic resonance imaging system. The method comprises:
providing an acquired MRI-Dataset comprising measurements of the heart over a predefined measuring-time period;
providing a trained deep learning network according to an embodiment of the invention;
creating input data based on and/or calculated from the acquired dataset and entering the input data into an input layer of the deep learning network; and outputting the results of the trained deep learning network.

A device according to an embodiment of the invention for (automatically) determining a cardiac phase in magnet resonance imaging can also be used for controlling a magnetic resonance imaging system. The device comprises:
a data interface designed for receiving an acquired MRI-Dataset comprising measurements of the heart over a predefined measuring-time period;
a trained deep learning network according to an embodiment of the invention;
an input-data-unit designed for creating input data based on and/or calculated from the acquired MRI dataset and entering the input data into an input layer of the deep learning network; and
an output unit designed for outputting the results of the trained deep learning network.

A control device according to an embodiment of the invention for controlling a magnetic resonance imaging system comprises a device according to an embodiment of the invention. Alternatively or additionally it is designed to perform the method according to an embodiment of the invention.

A magnetic resonance imaging system comprising a control device according to an embodiment of the invention.

At least one embodiment of the invention is also achieved by a computer program product with a computer program that is directly loadable into the memory of a computing system or a control device of a magnetic resonance imaging system, and which comprises program units to perform the steps of an embodiment of the inventive method when the program is executed by the control device or the computing system. In addition to the computer program, such a computer program product can also comprise further parts such as documentation and/or additional components, also hardware components such as a hardware key (dongle etc.) to facilitate access to the software.

A computer readable medium such as a memory stick, a hard-disk or other transportable or permanently-installed carrier can serve to transport and/or to store the executable parts of the computer program product so that these can be read from a processor unit of a control device or a computing system. A processor unit can comprise one or more microprocessors or their equivalents.

At least one embodiment of the invention is also directed to a trained deep learning network for determining a cardiac phase in magnet resonance imaging, comprising:
an input layer;
an output layer; and
a number of hidden layers, between the input layer and the output layer, the layers processing input data entered into the input layer, wherein the deep learning network is designed and trained to output results including a probability or some other label of a certain cardiac phase at a certain time in the input data entered.

At least one embodiment of the invention is also directed to a method for determining a cardiac phase in magnet resonance imaging, comprising:
providing an acquired MRI-Dataset including measurements of a heart over a measuring-time period;
providing a trained deep learning network including an input layer, an output layer, and a number of hidden layers, between the input layer and the output layer, the layers processing input data entered into the input layer;
creating input data, at least one of based on the acquired MRI-dataset and calculated from the acquired MRI-dataset, and entering the input data into the input layer of the deep learning network; and outputting results of the trained deep learning network corresponding to a probability or some other label of the cardiac phase at a time within the measuring-time period, based upon the input data entered.

At least one embodiment of the invention is also directed to a device for determining a cardiac phase in magnet resonance imaging, comprising:

a data interface, designed to receive an acquired MRI-Dataset including measurements of a heart over a measuring-time period;

the trained deep learning network of an embodiment;

an input-data-unit, designed to create input data at least one of based on the acquired MRI dataset and calculated from the acquired MRI dataset, and designed to enter the input data into an input layer of the deep learning network;

an output unit designed to output the results of the trained deep learning network.

At least one embodiment of the invention is also directed to a training method for manufacturing a deep learning network, comprising:

a) providing a deep learning network intended to be trained, the deep learning network being designed to output a probability or some other label of a certain cardiac phase at a time from input data;

b) providing multiple training-datasets, based on MRI-measurements of a heart over a measuring-time period and information about a cardiac phase at time points of each training-dataset of the multiple training-datasets as ground truth;

c) entering a training-dataset into an input layer of the deep learning network;

d) calculating a loss-value based on a difference between the output of the deep learning network and the information about the heart phase within a synchronized time;

e) adjusting parameters of the deep learning network;

f) repeating steps d) and e) until the loss-value suits a convergence criterium or a maximum number of repetitions is reached; and g) repeating steps c) to f) multiple times for different training-datasets.

At least one embodiment of the invention is also directed to a control device to control an MRI system, comprising: the device of an embodiment.

At least one embodiment of the invention is also directed to a magnetic resonance imaging system comprising: the control device of an embodiment.

At least one embodiment of the invention is also directed to a non-transitory computer program product storing a computer program, directly loadable into a computing system or a control device for a magnetic resonance imaging system, the program including program elements for performing the method of an embodiment when the computer program is executed by the computing system or the control device.

At least one embodiment of the invention is also directed to a non-transitory computer-readable medium storing program elements, readable and executable by a computer to perform the method of an embodiment when the program elements are executed by the computer.

BRIEF DESCRIPTION OF THE DRAWINGS

Other objects and features of the present invention will become apparent from the following detailed descriptions considered in conjunction with the accompanying drawings. It is to be understood, however, that the drawings are designed solely for the purposes of illustration and not as a definition of the limits of the invention.

FIG. 4 shows an example of the workflow with the deep learning network according to the method of an embodiment of the invention.

FIG. 5 shows a block diagram of the workflow of a preferred method according to an embodiment of the invention.

In the diagrams, like numbers refer to like objects throughout. Objects in the diagrams are not necessarily drawn to scale.

DETAILED DESCRIPTION OF THE EXAMPLE EMBODIMENTS

Figure 1:
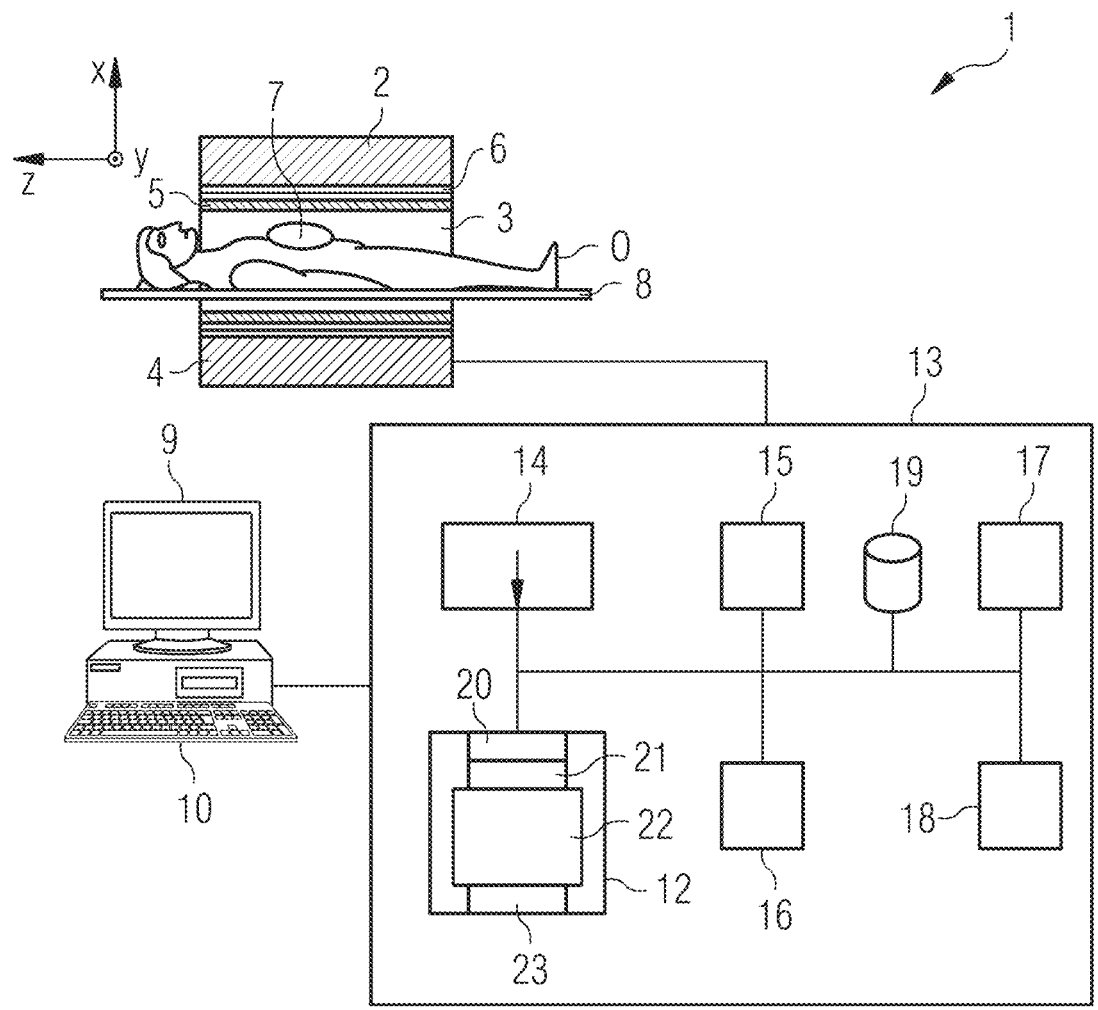
FIG. 1 shows a simplified MRI system according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A trained deep learning network according to an embodiment of the invention for determining a cardiac phase in magnet resonance imaging comprises an input layer, an output layer and a number of hidden layers between input layer and output layer and the layers processing input data entered into the input layer. The deep learning network is designed and trained to output a probability or some other label of a certain cardiac phase at a certain time from entered input data. This means that the output of the deep learning network is a probability in dependence on time or a label (i.e. the dependence) for certain time points of a dataset.

The expression "cardiac phase" refers to an individual state within the cardiac cycle (especially always the same state). Preferred phases (states) are the R-wave, the Q-wave, the S-wave or the T-wave. Preferably, the deep learning network can also be trained to distinguish between different states within a cardiac cycle.

The expression "deep learning network" here pertains to a device or software module based on deep (machine) learning. Deep learning is a special method of machine learning that is based on an artificial neural network with representation learning. Preferred deep learning networks are deep neural networks, deep belief networks, recurrent neural networks and convolutional neural networks. The term "network" indicates here that there could be a physical network, i.e. a network of physical nodes connected with signal lines (e.g. a FPGA or a network of physical computing devices). However, the term also means that there could be a virtual network based on virtual nodes (e.g. virtual neurons) connected with virtual signal lines (e.g. nodes linked with each other). Thus, the deep learning network could be present as physical (hardware) network in the form of a hardware module or as a virtual network in form of a software module, wherein the software module can be present in an individual (hardware) computing module.

The expression "other label" refers to an information concerning a cardiac phase, especially in addition with a certain probability. Although an R-wave is a preferred cardiac phase, an arbitrary phase or arbitrary phases could be chosen (wherein always the same phases are detected in the heartbeat). A label could be the label "R-wave" or "T-wave" to label certain points in time of the cardiac cycle. On the other Hand, the label could comprise probabilities, e.g. "85% probability for an R-wave". The labels could be used for further training of a neuronal network, e.g. for a classification problem. Then the used network should determine for a number of positions (e.g. each position) of the input sequence with which probability a certain phase (e.g. R-wave) is present. The classification could comprise binary values (e.g. "R-wave" and "no R-wave") or comprise more than two classes (e.g. "R-wave", "T-wave", . . . ). It is preferred that for each class, the network would provide a probability. Class and probability would be a preferred label.

Another preferred label could comprise a value of a (time-) distance at a certain point of a cardiac cycle to the nearest or next certain event (e.g. the distance to the last R-wave). At the point of the R-wave, the distance would be 0, at another point it would be the time to the last R-wave. It is preferred that a regression network is used to determine these labels.

Another preferred label could comprise a value for the intensity of a certain event (e.g. the "height" of the last or a determined R-wave). It is preferred that a regression network is used to determine a intensity value for the next event (e.g. an R-wave).

In the case of a virtual network, there are often artificial neurons present as elementary units in the network. An artificial neuron is a mathematical function conceived as a model of a biological neuron, receiving one or more inputs, that could e.g. represent excitatory postsynaptic potentials and inhibitory postsynaptic potentials at neural dendrites, and sums them to produce an output. Usually each input is separately weighted, and the sum is passed through a non-linear function known as an "activation function" (or "transfer function"). A preferred activation function has a sigmoid shape, but it may also take the form of other non-linear functions, piecewise linear functions, or step functions.

The deep learning network may have a well-known basic architecture. However, its inner structure and its performance is individually shaped after the training (so that it can determine the same relative position within the cardiac cycle in each heartbeat). Thus, it can be said that the training defines the inner "structure" of the deep learning network and distinguishes it from other trained deep learning networks (even of the same basic architecture).

Within its training phase, the weights or parameters within its structure are automatically adjusted to recognize features for the detection of cardiac phases, preferably by using a certain loss function and an optimization function.

The deep learning network has preferably been trained with multiple training-datasets, based on MRI-measurements of the heart over a predefined measuring-time period and information about a predefined cardiac phase at certain time points of each training-dataset as ground truth, by entering the training-datasets into an input layer of the deep learning network, calculating a loss-value for each training-dataset based on the difference between the output of the deep learning network and the information about the predefined heart phase within a synchronized time and adjusting parameters of the deep learning network until the loss-value is minimized.

An advantageous input to such a network can be a reasonably long continuous temporal window of a 1D Superior-Inferior (SI) projections as previously described. The output can be probabilities or other label for different classes of a cardiac cycle for every SI projection within the input window. A Superior-inferior projection produces advantageous results of a specific sequence and it is also a good choice for determining respiratory motion. However, for determining cardiac phase also other projections are possible, generally it is preferred to choose any k-space line passing through the center of k-space, even regardless of its direction.

In a simple example, the deep learning network can distinguish between two classes: "R-wave" vs. "no R-wave". This information can be used afterwards to bin the SI projections between two adjacent R-waves into different cardiac phases. In a more complicated model, the network can also be trained to distinguish between different states within a cardiac cycle: e.g. P-wave, R-wave, T-wave, and so on. For this, so called "ground-truth" data for the SI projections in the training data set is needed, e.g. a recorded ECG-signal or some other labels, classifying the state of one SI projection within a cardiac cycle.

Using these labels as ground-truth data, a deep learning network can be trained, with the previously described inputs and outputs. Architecture of such a network can comprise e.g. alternating convolutional and pooling layers, for the output layer e.g. a Sigmoid function can be used for the classification set-up. The convolutional layers extract the features, that are indicators for different positions within the cardiac cycle, pooling layers reduce the dimensionality.

It is preferred that pooling layers (or respective layers) are implemented that are designed to reduce only the spatial dimension of the input window of the SI projections, while maintaining the temporal dimension. This has the advantage that the output has the same temporal dimension as the input, but a lower spatial resolution, e.g. a spatial resolution of 1 (R-wave or no R-wave).

For the optimization of the weights/parameters of all layers, well-known optimization approaches, e.g. the Gradient Descent or Adam in combination with e.g. the cross entropy loss function can be used.

A training method according to an embodiment of the invention for manufacturing a deep learning network according to the invention, comprises:

a) Providing a deep learning network intended to be trained, wherein the deep learning network is designed to output a probability or other label of a certain cardiac phase at a certain time from input data. Appropriate deep learning networks are described above, e.g. a convolutional network, preferably comprising alternating convolutional and pooling layers and especially for the output layer a sigmoid function as activation function.

b) Providing multiple training-datasets, based on MRI-measurements of the heart over a predefined measuring-time period and information about a predefined cardiac phase at certain time points of each training-dataset as ground truth, the information especially based on ECG data. The information about the cardiac phase should name the cardiac phase present at respective time points of the training dataset. For example, ECG data is synchronized to the training data (showing the actual cardiac state at the time of measurement). At the time points there is a R-wave in the ECG data, the training data get an individual label for an R-wave. Of course, other waves can be labeled also or instead or the (synchronized) ECG data can be used as a label.

c) Entering a training-dataset into an input layer of the deep learning network. Of course, this must be done in a way that the deep learning network can process the training data and calculate an output. It is preferred that the training-dataset comprises a Superior-Inferior projection calculated from a central k-line of an acquired MRI-dataset over a predefined time period.

At the beginning of the training, the output won't be very accurate. However, due to the ground-truth labels the system "knows" whether the output is right or not, i.e. the system can calculate an output, e.g. based on a loss function, and can compare this output with a certain ground truth. This knowledge can be used for the next step.

d) Calculating a loss-value based on the difference between the output of the deep learning network and the information about the predefined heart phase within a synchronized time from the ground-truth. This loss value can e.g. be a digital value of "right" or "wrong", but also any other value reflecting the quality of the output in the light of the ground truth.

e) Adjusting parameters of the deep learning network. To configure the deep learning network, its parameters (at least in the hidden layers) have to be configured "correctly". The training is used to adjust these parameters by using a vast set of training data. With adjusted parameters it can be tested, if the loss-value is better or not.

f) Repeating steps d) and e) until the loss-value suits a convergence criterium (e.g. is below a predefined threshold) or the maximum number of repetitions is reached. Thus, the loss value is calculated again with adjusted parameters until it is minimized. An indicator for a minimization could be defined with the convergence criterium.

g) Repeating steps c) to f) multiple times for different training-datasets. The above "loop" of steps d), e) and f) is now processed for many different datasets. This results in a desired adjustment of the parameters what is equivalent to a trained deep learning network.

After the training, the weights/parameters of the network are adapted for the specific task and can e.g. detect the R-waves from previously unseen continuous measurements.

Therefore, with such trained deep learning network the actual task can be solved, i.e. the automatic determination of a cardiac phase (or different cardiac phases) in magnet resonance imaging.

A method according to an embodiment of the invention for (automatically) determining a cardiac phase in magnet resonance imaging can also be used for controlling a magnetic resonance imaging system. The method comprises:

Providing an acquired MRI-Dataset comprising measurements of the heart over a predefined measuring-time period. Since a cardiac phase should be determined, the MRI signal should comprise signals of the heart. This could e.g. be achieved with a cardiac coil. The MRI signals should be recorded with a coil arrangement also used for the training dataset, however, depending on the training (e.g. with many different coil arrangements) the trained deep learning network could be rendered robust enough to work with arbitrary coil arrangements. The acquired MRI-Dataset can have an arbitrary size, e.g. can be a data stream. The coils are typically part of the RF reception antenna system of an MRI device.

Providing a trained deep learning network according to an embodiment of the invention.

Creating input data based on and/or calculated from the acquired dataset and entering the input data into an input layer of the deep learning network. This input data should have the shape of the training data. In the case, the deep learning network has been trained with raw MRI-data, the input data can also be raw data. However, it is preferred to use 1D-SI projections for input data (as described above in the case of the training data). It should be noted that each input data can also be used as training data for further train the deep learning network as long as there can be derived a ground truth for this input data.

The input data may be a data stream, but it is preferred that it has a predefined temporal length. In the case, the temporal length of the MRI-dataset is longer than this predefined length, the input data may comprise temporal bits of the MRI dataset, wherein temporally following input data may overlap.

Outputting the results of the trained deep learning network. The trained deep learning network will automatically process the entered input data and produce an output. This output will comprise (or be) a probability or other label of a certain cardiac phase (e.g. for an R-wave).

A device according to an embodiment of the invention for (automatically) determining a cardiac phase in magnet resonance imaging can also be used for controlling a magnetic resonance imaging system. The device comprises the following components:

A data interface designed for receiving an acquired MRI-Dataset comprising measurements of the heart over a predefined measuring-time period. Such data interfaces are well known.

A trained deep learning network according to an embodiment of the invention. This trained deep learning network can be a hardware device or a software module executed in a computing unit that is then counted as hardware component of the trained deep learning network.

An input-data-unit designed for creating input data based on and/or calculated from the acquired MRI dataset and entering the input data into an input layer of the deep learning network. This input-data-unit can be part of a computing unit as mentioned above or of a hardware unit being the trained deep learning network and may comprise a (hardware or virtual) data bus or another data interface for entering the input data into the input layer.

An output unit designed for outputting the results of the trained deep learning network. Such output units are well known.

Thus, at least one embodiment of the invention proposes a deep learning based approach which is able to identify a cardiac phase and, therefore, allows the retrospective cardiac binning of continuously acquired data without an external signal or hand-crafted/a priori known feature selection. The input to this network can be e.g. a two-dimensional signal, which is a continuous, temporal window of 1D-SI projections. This window should be big enough to contain at least one cardiac cycle, e.g. 2 or 3 seconds of the measurement. The output of the network could be a prediction for every timepoint t (every 1D-SI projection) within this input window. This prediction can e.g. be a class probability, describing whether there is a R-wave existent at this timepoint t or not.

This way, every acquired data point (every k-space line) in the measurement is associated with at least one cardiac phase and can be used for the dynamic reconstruction of these cardiac phases. The utilization of this neural network would eliminate the need of an external ECG-signal acquisition or post-processing the data with hand-crafted features and a priori knowledge using e.g. a PCA or ICA approach.

A preferred deep learning based workflow for the detection of R-wave positions from continuous measurements is explained in the following: A temporal window of 1D-SI projections from acquired MRI data is used as input data for the network, which performs classification (e.g. binary "R-wave"/"no R-wave" or multiple phases of the ECG cycle) or regression (e.g. probability of R-wave, synthetic ECG curve) for every 1D-SI projection. Thus, the 1D-SI projections from the acquired central k-space readouts are the basis for the input data for the trained deep learning network, which can predict the class or either the state of a SI projection within a cardiac cycle. These predictions can be used afterwards for a retrospective temporal binning of the data.

The SI projections are forward passed through the network, which outputs the cardiac state or the probability or other label for a particular event (e.g. R-wave) within a cardiac cycle. The same cardiac phase can then be assigned to all subsequent k-space lines, belonging to this k-space center readout as the processed 1D-SI projection. This output can then be used for retrospective binning of the data and for reconstruction of dynamic data sets with different cardiac phases.

A control device according to an embodiment of the invention for controlling a magnetic resonance imaging system comprises a device according to an embodiment of the invention. Alternatively or additionally it is designed to perform the method according to an embodiment of the invention.

The control device may comprise additional units or devices for controlling components of a magnetic resonance imaging system, e.g. a sequence control unit for measurement sequence control, a memory, a radio-frequency transmission device that generates, amplifies and transmits RF pulses, a gradient system interface, a radio-frequency reception device to acquire magnetic resonance signals and/or a reconstruction unit to reconstruct magnetic resonance image data.

A magnetic resonance imaging system comprising a control device according to an embodiment of the invention.

Some units or modules of the device or the control device mentioned above can be completely or partially realized as software modules running on a processor of a computing system or a control device. A realization largely in the form of software modules can have the advantage that applications already installed on an existing system can be updated, with relatively little effort, to install and run these units of the present application.

At least one embodiment of the invention is also achieved by a computer program product with a computer program that is directly loadable into the memory of a computing system or a control device of a magnetic resonance imaging system, and which comprises program units to perform the steps of an embodiment of the inventive method when the program is executed by the control device or the computing system. In addition to the computer program, such a computer program product can also comprise further parts such as documentation and/or additional components, also hardware components such as a hardware key (dongle etc.) to facilitate access to the software.

A computer readable medium such as a memory stick, a hard-disk or other transportable or permanently-installed carrier can serve to transport and/or to store the executable parts of the computer program product so that these can be read from a processor unit of a control device or a computing system. A processor unit can comprise one or more microprocessors or their equivalents.

Particularly advantageous embodiments and features of the invention are given by the claims, as revealed in the following description. Features of different claim categories may be combined as appropriate to give further embodiments not described herein.

As indicated above, a preferred trained deep learning network is trained to process results based on raw MRI data as input data, especially a number of k-lines. Additionally or alternatively, a preferred trained deep learning network is trained to process results based on reconstructed data as input data, especially a Superior-Inferior projection as described above.

According to a preferred (trained) deep learning network, the hidden layers comprise alternating convolutional layers and pooling layers. It is preferred that for the output layer a sigmoid function is used as transfer function (activation function).

According to a preferred method, the input data is calculated from the acquired MRI-dataset by the use of a Superior-Inferior projection applied on a number of k-lines over a predefined time period. This has been already described above. The SI projection is preferably based on at least the central k-line of the acquired MRI-dataset, and especially is based only on this central k-line. The central k-line is the line with kx=0 and ky=0 or at least the k-line nearest kx=0 and ky=0.

According to a preferred method, the acquired MRI-dataset comprises data from a cardiac coil. As indicated above, with a cardiac coil the signal of the heartbeat can be measured accurately.

According to a preferred method, the input layer of the trained deep learning network comprises a number of input nodes and the acquired MRI-dataset comprises a number of coil-datasets from a multiplicity of coils. The number of coil-datasets should at least match the number of input nodes. Preferably in the case when the number of coil-datasets is bigger than the number of input nodes, the coil-datasets are preferably transformed in a number of channel datasets (i.e. the input data) corresponding with the number of input nodes, preferably wherein each channel dataset (input data) is assigned to one individual input node. A preferred transformation is a SVD-transformation (SVD: Singular Value Decomposition). For example, for 30 Coils, an SVD transformation for the 30 coil datasets into a smaller number of input nodes (e.g. 3 input nodes) is calculated, wherein preferably the coil data with the biggest variation are summed up.

According to a preferred method, the acquired MRI-dataset or the input data is temporally segmented into input segments, wherein temporally adjacent input segments preferably (temporally) overlap with another, wherein these input segments are entered into the input layer of the trained deep learning network. Preferably, for training and/or for normal workflow, a temporal window is defined (for a predefined time period) and input data is designed to fit this window. Such window may "slide" over an MRI dataset or a SI-projection to "cut" out segments as input data. The segments can overlap with another, but they do not have to. If e.g. the input time dimension of the network is 3 s of data, and a measurement is 20 s of data, then e.g. the last segment of input data can overlap with the second-to-last segment and the other segments could not overlap. However, overlaps are advantageous to reduce false results just because the relevant position just lies at the edge of a segment.

According to a preferred method, based on the results of the trained deep learning network an acquired MRI-Dataset is automatically segmented into a number of subsets, preferably wherein the segmentation is based on a predefined segmentation of the cardiac cycle into temporal bins and wherein data of the acquired MRI-Dataset within the same cardiac cycle is particularly preferably segmented into temporal bins depending on the actual phase of the heart in the data.

Thus, using the determined "labels" (e.g. probabilities) for a cardiac phase, the 1D-SI projections can be binned into a desired quantity of cardiac phases (e.g. between two adjacent detected R-waves or other waves), and a cardiac phase of every 1D-SI projection can be used for the subsequent acquired k-space lines up to the next center readout and thus, the next 1D-SI projection.

In a preferred device according to an embodiment of the invention, components of the device are part of a data-network, wherein preferably the data-network and a magnetic resonance imaging system which provides image data) are in data-communication with each other, wherein the data-network preferably comprises parts of the internet and/or a cloud-based computing system, wherein preferably the device according to an embodiment of the invention or at least the deep learning network is realized in this cloud-based computing system. For example, the components of the device are part of a data-network, wherein preferably the data-network and a medical imaging system which provides the image data are in communication with each other. Such a networked solution could be implemented via an internet platform and/or in a cloud-based computing system.

The method may also include elements of "cloud computing". In the technical field of "cloud computing", an IT infrastructure is provided over a data-network, e.g. a storage space or processing power and/or application software. The communication between the user and the "cloud" is achieved by way of data interfaces and/or data transmission protocols.

In the context of "cloud computing", in a preferred embodiment of the method according to the invention, provision of data via a data channel (for example a data-network) to a "cloud" takes place. This "cloud" includes a (remote) computing system, e.g. a computer cluster that typically does not include the user's local machine. This cloud can be made available in particular by the medical facility, which also provides the medical imaging systems. In particular, the image acquisition data is sent to a (remote) computer system (the "cloud") via a RIS (Radiology Information System) or a PACS (Picture Archiving and Communication System).

Within the scope of a preferred embodiment of the device according to the invention, the abovementioned units, especially the deep learning network, are present on the "cloud" side. A preferred device further comprises, a local computing unit connected to the device via a data channel (e.g. a data-network, particularly configured as RIS or PACS). The local computing unit includes at least one data receiving interface to receive data. Moreover, it is preferred if the local computer additionally has a transmission interface in order to send data to the device.

At least one embodiment of the invention facilitates replacing the prior methodologies for detection or acquisition of R-waves/ECG-signals with a trained deep learning network. The main advantages of the proposed method based on deep learning compared to previous methods are first hand, that no more external ECG-signal acquisition with external devices is needed simultaneously and additionally to the MR signal itself, and second, the features describing the cardiac movement within the 1D-SI projections do not have to be derived using frequency filtering and other methods. Methods based on frequency filtering and ICA/PCA often suffer from unclean 1D-SI projections, e.g.

noise or trajectory-dependent imperfections, that have influence on the data and have to be removed, before deriving the R-wave positions (or more general the same relative positions within the cardiac cycle in each heartbeat), as otherwise they can have influence on the subsequent computations. Using a deep learning based technique, the noise or other influences do not have to be removed from the data prior to the network processing using filters with adjusted parameters, as the network is able to learn the extraction of stable features automatically.

Furthermore, using frequency filtering to extract the motion curves from computed main independent or principal components, the typical cardiac frequency must be known a priori. This can be problematic for especially patients with arrythmia, who do not have a regular cardiac frequency, and thus, one specific cardiac frequency cannot be discovered for these cases. Using our deep learning approach, this is no longer needed and no other a prior knowledge is incorporated. The deep learning network can learn features, that belong to e.g. an R-wave independently of a specific frequency.

Furthermore, the processing with a deep neural network is very fast (e.g. in the range of milliseconds for one forward pass), while methods based on PCA or ICA can incorporate optimization techniques, which can be long-lasting. Using this technique in a clinical workflow can replace the need for external sensors for acquiring the ECG-signal, as well as the need for post-processing methods for the derivation of different cardiac phases from 1D-SI projections and enabling an ECG-free cardiac continuously acquired scans.

FIG. 1 shows a schematic representation of a magnetic resonance imaging system 1 ("MRI-system"). The MRI system 1 includes the actual magnetic resonance scanner (data acquisition unit) 2 with an examination space 3 or patient tunnel in which a patient or test person is positioned on a driven bed 8, in whose body the actual examination object is located.

The magnetic resonance scanner 2 is typically equipped with a basic field magnet system 4, a gradient system 6 as well as an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil can also be used as an RF reception antenna system, and the local coils can respectively be switched into different operating modes.

The basic field magnet system 4 is designed that images of the heart can be recorded. It here is designed in a typical manner so that it generates a basic magnetic field in the longitudinal direction of the patient, i.e. along the longitudinal axis of the magnetic resonance scanner 2 that proceeds in the z-direction. The gradient system 6 typically includes individually controllable gradient coils in order to be able to switch (activate) gradients in the x-direction, y-direction or z-direction independently of one another.

The MRI system 1 shown here is a whole-body system with a patient tunnel into which a patient can be completely introduced. However, in principle the invention can also be used at other MRI systems, for example with a laterally open, C-shaped housing, as well as in smaller magnetic resonance scanners in which only one body part can be positioned.

Furthermore, the MRI system 1 has a central control device 13 that is used to control the MRI system 1. This central control device 13 includes a sequence control unit 14 for measurement sequence control. With this sequence control unit 14, the series of radio-frequency pulses (RF pulses) and gradient pulses can be controlled depending on a selected pulse sequence Different control protocols for different measurements or measurement sessions are typically stored in a memory 19 and can be selected by and operator (and possibly modified as necessary) and then be used to implement the measurement.

To output the individual RF pulses of an pulse sequence, the central control device 13 has a radio-frequency transmission device 15 that generates and amplifies the RF pulses and feeds them into the RF transmission antenna system 5 via a suitable interface (not shown in detail). To control the gradient coils of the gradient system 6, the control device 13 has a gradient system interface 16. The sequence control unit 14 communicates in a suitable manner with the radio-frequency transmission device 15 and the gradient system interface 16 to emit the pulse sequence.

Moreover, the control device 13 has a radio-frequency reception device 17 (likewise communicating with the sequence control unit 14 in a suitable manner) in order to acquire magnetic resonance signals (i.e. raw data) for the individual measurements, which magnetic resonance signals are received in a coordinated manner from the RF reception antenna system 7 within the scope of the pulse sequence.

A reconstruction unit 18 receives the acquired raw data and reconstructs magnetic resonance image data (an MRI dataset) therefrom for the measurements. This reconstruction is typically performed on the basis of parameters that may be specified in the respective measurement or control protocol. For example, the image data can then be stored in a memory 19.

Operation of the central control device 13 can take place via a terminal 10 with an input unit and a display unit 9, via which the entire MRI system 1 can thus also be operated by an operator. MR images can also be displayed at the display unit 9, and measurements can be planned and started via the input unit (possibly in combination with the display unit 9), and in particular suitable control protocols can be selected (and possibly modified) with suitable series of pulse sequence as explained above.

The control device 13 comprises a device 12 designed to perform the method according to an embodiment of the invention. This device 12 comprises the following components that may appear to be software modules.

A data interface 20 designed for receiving an acquired MRI-Dataset RD, for example raw data RD or reconstructed image data, comprising measurements of the heart over a predefined measuring-time period.

A trained deep learning network 22 as further described in the following examples.

An input-data-unit 21 designed for creating input data ID, e.g. an SI projection, based on and/or calculated from the acquired MRI dataset RD and for entering the input data ID into an input layer of the deep learning network 22.

An output unit 23 designed for outputting the results of the trained deep learning network 22.

The MRI system 1 according to an embodiment of the invention, and in particular the control device 13, can have a number of additional components that are not shown in detail but are typically present at such systems, for example a network interface in order to connect the entire system with a network and be able to exchange raw data and/or image data or, respectively, parameter maps, but also additional data (for example patient-relevant data or control protocols).

The manner by which suitable raw data are acquired by radiation of RF pulses and the generation of gradient fields, and MR images are reconstructed from the raw data, is known to those skilled in the art and thus need not be explained in detail herein.

Figure 2:
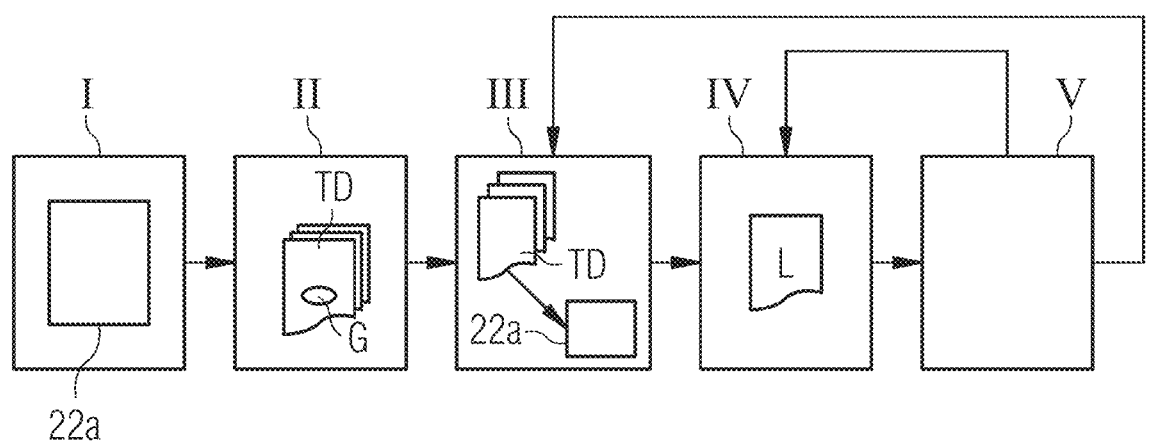
FIG. 2 shows a block diagram of the process flow of a preferred training method according to an embodiment of the invention.
Figure 3:
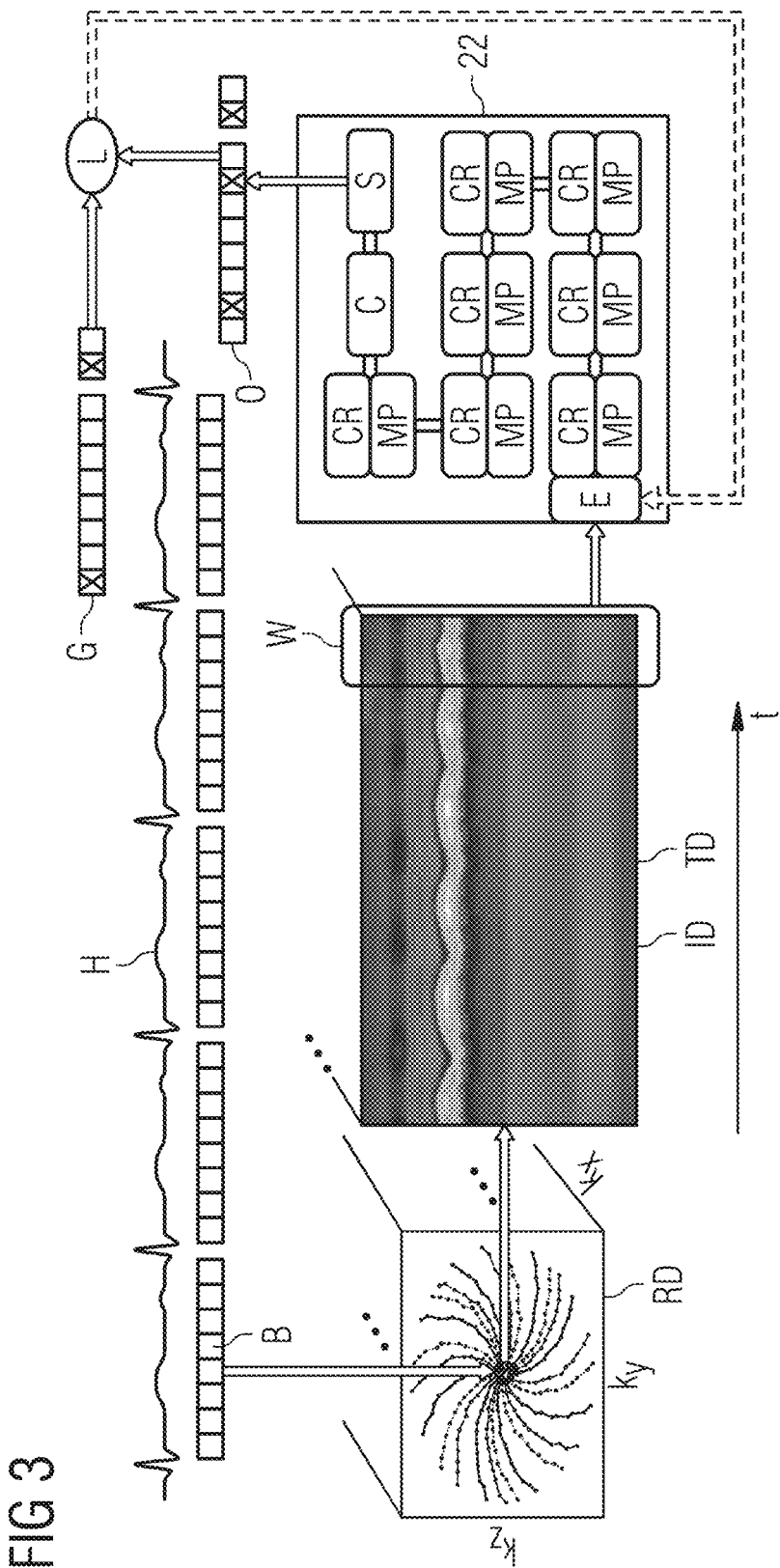
FIG. 3 shows an example of the function and the training of the deep learning network according to an embodiment of the invention.

FIG. 2 shows a block diagram of the process flow of a preferred training method according to an embodiment of the invention for manufacturing a deep learning network 22.

In step I, a deep learning network intended to be trained 22a is provided, wherein the deep learning network 22a is designed to output a probability or other label of a certain cardiac phase at a certain time from input data ID.

In step II, multiple training-datasets TD are provided, based on MRI-measurements of the heart over a predefined measuring-time period and information about a predefined cardiac phase at certain time points of each training-dataset as ground truth G, the information especially based on ECG data.

In step III, a training-dataset TD is entered into an input layer of the deep learning network 22, preferably wherein the training-dataset TD comprises a Superior-Inferior projection calculated from a central k-line of an acquired MRI-dataset RD over a predefined time period.

In step IV, a loss-value L is calculated based on the difference between the output OD of the deep learning network 22 and the information about the predefined heart phase within a synchronized time.

In step V, parameters of the deep learning network 22 are adjusted.

After Step V there are two convoluted loops, an inner loop and an outer loop.

In the inner loop, steps IV and V are repeated until the loss-value L suits a convergence criterion or a maximum number of repetitions is reached.

In the outer loop, compassing the inner loop, steps III to V with the inner loops are repeated multiple times for different training-datasets TD. Thus, for any training dataset TD the parameters are adjusted several times to adjust parameters with a series of loss values L. Thus, the inner loop runs over datasets and the outer loop runs over epochs (inner loops).

In this example, a spiral spoke sampling scheme is used as an example for a segmented 3-D acquisition. The acquired MRI dataset RD comprises data in such spiral spoke sampling schemes in k-space (kx, ky, kz) over a time period for at least 2 or 3 seconds (or a continuous measurement over several seconds or minutes). The cartesian phase-encoding plane is shown left, which is incoherently undersampled. Every first central spiral spoke k-space readout (1D inverse Fourier transformed, marked with arrows) is used as a 1D-SI projection what is the input data ID or (in the course of training) the training dataset TD. A training dataset TD comprises input data ID that are used for training.

A continuous, temporal window W of multiple 1D-SI projections is used as input data ID to the deep learning network 22.

The deep learning network 22 here comprises an input layer E, an output layer S with a sigmoid function S as transfer function (or activation function) and several hidden layers, wherein seven of the hidden layers comprise a combination of a convolution layer with a rectified linear unit ("ReLU") CL followed by a max pooling layer ML and the eighth hidden layer comprises a convolution layer C. Such general architectures are known for convolutional networks. Preferably, a fully convolutional neural network (FCN) with overall 8 layers is used: Every convolutional layer is followed by a Max-Pooling, reducing spatial dimensionality while preserving temporal resolution.

The deep learning network is trained in a supervised manner using ground-truth G labels (see FIG. 2) from an acquired ECG-signal from an external ECG device. A heartbeat H symbolizing the real heartbeat as well as an ECG signal can be found at the top of the figure. A suitable label for detecting R-waves can be a binary label (e.g. 1="R-wave", R-wave").

After one forward pass, the current output of the network is compared with the ground-truth G labels, and a loss-value is calculated. In this example, the ground truth is symbolized with crosses in boxes representing temporal bins. Here the left line of boxes pointing with an arrow to the loss-value L is the ground truth and the lower line of boxes pointing with an arrow to the loss-value L are the output data O. To extract the class labels from the raw output of the deep learning network 22 during testing, maximum values from every detected R-wave can be taken.

It can be seen that there are two incorrect crosses and one empty box where there should have been a cross (R-wave found). Thus, the loss-value L is bad and, therefore, backwarded into the network to adjust the network weights (i.e. the parameters) to achieve better output data O.

This process is repeated until a convergence criterium or the maximum number of repetitions is reached.

Below the heartbeat H a series of boxes is shown that represent temporal bins B. Between each R-wave, there are eight boxes. Thus, the time between two R-waves can be divided by eight and MRI-data can be sorted into temporal bins B depending on the time of measurement. Thus, using the predictions of the deep learning network, data can be binned into a desired quantity of cardiac phases between two adjacent R-waves.

FIG. 4 shows an example of the workflow with the deep learning network 22 according to an embodiment of the invention. For the network input, the MRI data of the different coils of an MRI-system 1 (see e.g. FIG. 1) can be reconstructed into 1D-SI projections of coil data CD. Then, the coil data CD can be preprocessed to provide data of same dimensions: For example, the 1D-SI projections can be cropped or interpolated to the same spatial and temporal resolutions, and converted to the same number of channels, e.g. by compressing the coils to the same amount for every scan by using an SVD-algorithm (SVD: Singular Value Decomposition). The coils are typically part of the RF reception antenna system 7 (see FIG. 1).

As shown above, the structure of the exemplary deep learning network 22 comprises here seven blocks with Convolution (3×3 kernel)—Rectified Linear Units (ReLU)—MaxPooling (3×2 kernel), each increasing the number of feature maps and reducing the spatial resolution by factor two. The last 1×1 convolution block maps the features to one class predicting the probability of a R-wave, followed by a Sigmoid function as output layer.

Afterwards, the output is for example thresholded at and the maximum values are taken from every detected R-wave for the exact positions. The output data OD show a plot of R-wave probability (top), probabilities above and below (middle) and maxima of the probabilities (bottom).

For example, MDI data is acquired during free-breathing using a 3D volume-selective, ECG-gated, prototype balanced Steady-StateFree-Precession sequence in short-axis orientation on a 1.5T scanner. Incoherent subsampling with a spiral spokes pattern is applied to the cartesian phase-encoding plane.

The 1D inverse Fourier-transformed lines of each k-space center readout (SI projections) are used as input samples (for workflow or training). For training, a simultaneously acquired ECG signal is used as ground-truth R-wave positions.

Then, SI projections are divided into continuous windows, each containing multiple and different number of R-wave labels depending on the R-R interval of the examined heart. For example, here all (training) input data can be different in terms of spatial and temporal resolution as well as number of receiver coils, following preprocessing is applied (resulting e.g. in 128×64×10 sized input samples:

(1) Temporal interpolation to a fixed size of 64 SI projections for every window;
(2) Cropping of every SI projection to a fixed spatial resolution (128);
(3) Compression of the different coil channels to e.g. ten channels using SVD; and
(4) Normalization between 0 and 1.

FIG. 5 shows a block diagram of the workflow of a preferred method according to an embodiment of the invention for determining a cardiac phase in magnet resonance imaging.

In step Ia, an acquired MRI-Dataset RD is provided comprising measurements of the heart over a predefined measuring-time period.

In step IIa, a trained deep learning network 22 according to an embodiment of the invention is provided.

In step IIIa, input data ID is provided based on and/or calculated from the acquired MRI-dataset RD and entered into an input layer E of the deep learning network 22.

In step IVa, the results of the trained deep learning network 22 are outputted.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other steps or elements. The mention of a "unit" or a "device" does not preclude the use of more than one unit or device.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A trained deep learning network for determining a cardiac phase in magnetic resonance imaging (MRI), the trained deep learning network comprising:
an input layer;
an output layer; and
a number of hidden layers between the input layer and the output layer, the hidden layers configured to process input data entered into the input layer,
wherein the trained deep learning network is configured to output results including at least one of a probability or a label of a certain cardiac phase at a certain time in the input data entered,
wherein the input data is MRI k-space data, and
wherein the trained deep learning network is configured to process the results based on the MRI k-space data.

2. The trained deep learning network of claim 1, wherein the hidden layers comprise alternating convolutional layers and pooling layers.

3. The trained deep learning network of claim 2, wherein the output layer includes a sigmoid function configured to be used as a transfer function.

4. A device for determining a cardiac phase in magnetic resonance imaging (MRI), the device comprising:
the trained deep learning network of claim 1;
a data interface configured to receive an acquired MRI k-space dataset including measurements of a heart over a measuring-time period; and
processing circuitry configured to cause the device to
create the input data at least one of based on the acquired MRI k-space dataset or calculated from the acquired MRI k-space dataset,
enter the input data into an input layer of the trained deep learning network, and
output the results of the trained deep learning network.

5. A control device to control magnetic resonance imaging (MRI) system, the control device comprising:
the device of claim 4.

6. A magnetic resonance imaging system comprising:
the control device of claim 5.

7. The trained deep learning network of claim 1, wherein the MRI k-space data includes at least one of a number of k-lines, reconstructed data, or a Superior-Inferior projection, as input data.

8. A method for determining a cardiac phase in magnetic resonance imaging (MRI), the method comprising:
acquiring an MRI k-space dataset including measurements of a heart over a measuring-time period;
creating input data, at least one of based on the acquired MRI k-space dataset or calculated from the acquired MRI k-space dataset;

entering the input data into an input layer of a trained deep learning network, the trained deep learning network including the input layer, an output layer, and a number of hidden layers between the input layer and the output layer, the hidden layers configured to process the input data entered into the input layer; and outputting results of the trained deep learning network corresponding to at least one of a probability or a label of the cardiac phase at a time within the measuring-time period, based upon the input data entered.

9. The method of claim 8, further comprising:
calculating the input data from the acquired MRI k-space dataset using a Superior-Inferior projection applied on a number of k-lines over a time period.

10. The method of claim 9, wherein the calculating the input data includes using the Superior-Inferior projection applied only on a central k-line of the acquired MRI k-space dataset.

11. The method of claim 9, wherein the acquired MRI k-space dataset includes data from a cardiac coil.

12. The method of claim 8, wherein the acquired MRI k-space dataset includes data from a cardiac coil.

13. The method of claim 8, wherein the input layer of the trained deep learning network includes a number of input nodes,
wherein the acquired MRI k-space dataset includes a number of coil-datasets from a multiplicity of coils, and
wherein the number of coil-datasets is greater than or equal to the number of input nodes.

14. The method of claim 13, wherein the number of coil-datasets is greater than the number of input nodes, the method further comprising:
transforming the coil-datasets in a number of input datasets corresponding with the number of input nodes.

15. The method of claim 14, further comprising:
assigning each input dataset to one individual input node of the number of input nodes.

16. The method of claim 8, further comprising:
temporally segmenting the acquired MRI k-space dataset or the input data into input segments.

17. The method of claim 16, wherein temporally adjacent input segments overlap with one another, the method further comprising:
entering the temporally adjacent input segments into the input layer of the trained deep learning network.

18. The method of claim 8, further comprising:
segmenting an acquired MRI k-space dataset into a number of subsets based on the results of the trained deep learning network.

19. The method of claim 18, wherein the segmenting includes segmenting the acquired MRI k-space dataset into temporal bins based on a segmentation of a cardiac cycle.

20. The method of claim 19, wherein the segmenting includes segmenting data of the acquired MRI k-space dataset within a same cardiac cycle into temporal bins depending on an actual phase of the heart in the data.

21. A non-transitory computer program product storing a computer program, loadable into a computing system or a control device for a magnetic resonance imaging system, the program including program elements for performing the method of claim 8 when the computer program is executed by the computing system or the control device.

22. A non-transitory computer-readable medium storing program elements, readable and executable by a computer to perform the method of claim 8 when the program elements are executed by the computer.

23. A training method for manufacturing a deep learning network, the method comprising:
a) providing a deep learning network intended to be trained, the deep learning network configured to output at least one of a probability or a label of a certain cardiac phase at a time from input data;
b) providing multiple training-datasets, based on magnetic resonance imaging (MRI)-k-space measurements of a heart over a measuring-time period and information about a cardiac phase at time points of each training-dataset of the multiple training-datasets;
c) entering a training-dataset of the multiple training datasets into an input layer of the deep learning network;
d) calculating a loss-value based on a difference between the output of the deep learning network and the information about the cardiac phase within a synchronized time;
e) adjusting parameters of the deep learning network;
f) repeating steps d) and e) until the loss-value suits a convergence criterium or a maximum number of repetitions is reached; and
g) repeating steps c) to f) multiple times for different training-datasets.

24. A non-transitory computer program product storing a computer program, loadable into a computing system or a control device for a magnetic resonance imaging system, the program including program elements for performing the method of claim 23 when the computer program is executed by the computing system or the control device.

25. A non-transitory computer-readable medium storing program elements, readable and executable by a computer to perform the method of claim 23 when the program elements are executed by the computer.

26. The training method of claim 23, wherein the information is based on ECG data.

27. The training method of claim 23, wherein the training-dataset includes a Superior-Inferior projection calculated from a central k-line of an acquired MRI k-space dataset over a time period.

* * * * *